United States Patent [19]

Dunham et al.

[11] Patent Number: 4,605,618

[45] Date of Patent: Aug. 12, 1986

[54] METHOD FOR MEASURING ANTI-INFLAMMATORY PROPERTIES OF A COMPOSITION

[75] Inventors: Philip B. Dunham, Syracuse; Gerald Weissmann, New York, both of N.Y.

[73] Assignees: New York University, New York; Syracuse University, Syracuse, both of N.Y.; Marine Biological Laboratory, Woods Hole, Mass.

[21] Appl. No.: 512,629

[22] Filed: Jul. 11, 1983

[51] Int. Cl.$^4$ .................. C12Q 1/02; G01N 21/59; G01N 33/48

[52] U.S. Cl. .................. 435/29; 73/64.1; 356/442; 436/63; 436/164; 436/183

[58] Field of Search .............. 422/73; 436/501, 63, 436/2, 164, 183; 435/29, 39; 73/64.1, 53; 356/36, 442, 436

[56] References Cited

U.S. PATENT DOCUMENTS

| | | | |
|---|---|---|---|
| 3,874,853 | 4/1975 | Byrnes | 436/164 |
| 3,923,459 | 12/1975 | Ertingshausen et al. | 436/164 |
| 4,252,536 | 2/1981 | Kishimoto et al. | 356/36 |
| 4,329,152 | 5/1982 | Lauwerys et al. | 422/73 |

FOREIGN PATENT DOCUMENTS

| | | | |
|---|---|---|---|
| 1006006 | 3/1977 | Canada | 436/164 |
| 0003639 | 9/1967 | Japan | 436/164 |

OTHER PUBLICATIONS

Rice et al., "Two $Ca^{2+}$ Functions are Demonstrated by the Substitution of Specific Divalent and Lanthanide Cations for the $Co^{2+}$ Required by the Aggregation Factor Complex from the Marine Sponge, Microclone Prolifera" *The Journal of Biological Chemistry* 258(10), 6394–9, 1983.

Rich, Abby M. et al., "Calcium Dependent Aggregation of Marine Sponge Cells is Provoked by Leukotriene $B_4$ and Inhibited by Inhibitors of Arachidonic Acid Oxidation," 1984, *Biochem. Biophys. Res. Commun.*, 121(3), 863–70.

Misevic, et al., "Cell Binding Fragments from a Sponge Proteoglycen-Like Aggregation Factor," *The Journal of Biological Chemistry* 257(12), 6931–6, 1982.

*Primary Examiner*—Arnold Turk
*Assistant Examiner*—Robert J. Hill, Jr.
*Attorney, Agent, or Firm*—Darby & Darby

[57] ABSTRACT

Disclosed is a method for measuring aggregation in sponge cells using a clinical aggregometer. In addition, using the marine sponge cell as an in vitro model for neutrophil aggregation, a method to determine the relative anti-inflammatory properties of non-steroidal anti-inflammatory pharmaceutical agents by clinical aggregometry is also disclosed.

6 Claims, 3 Drawing Figures

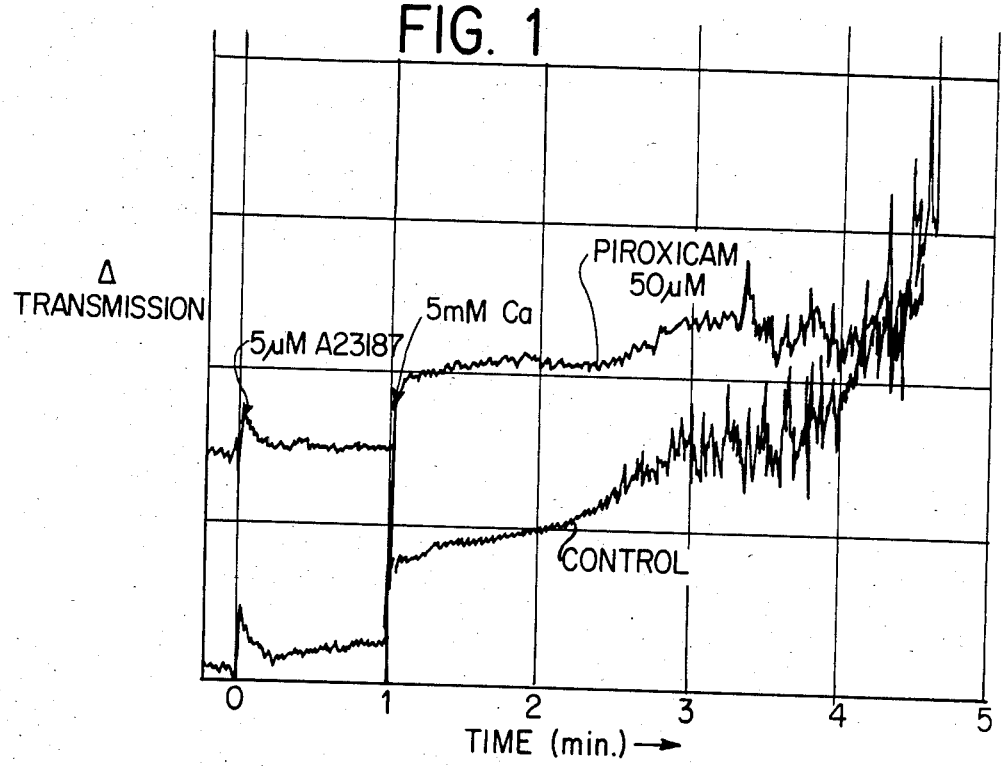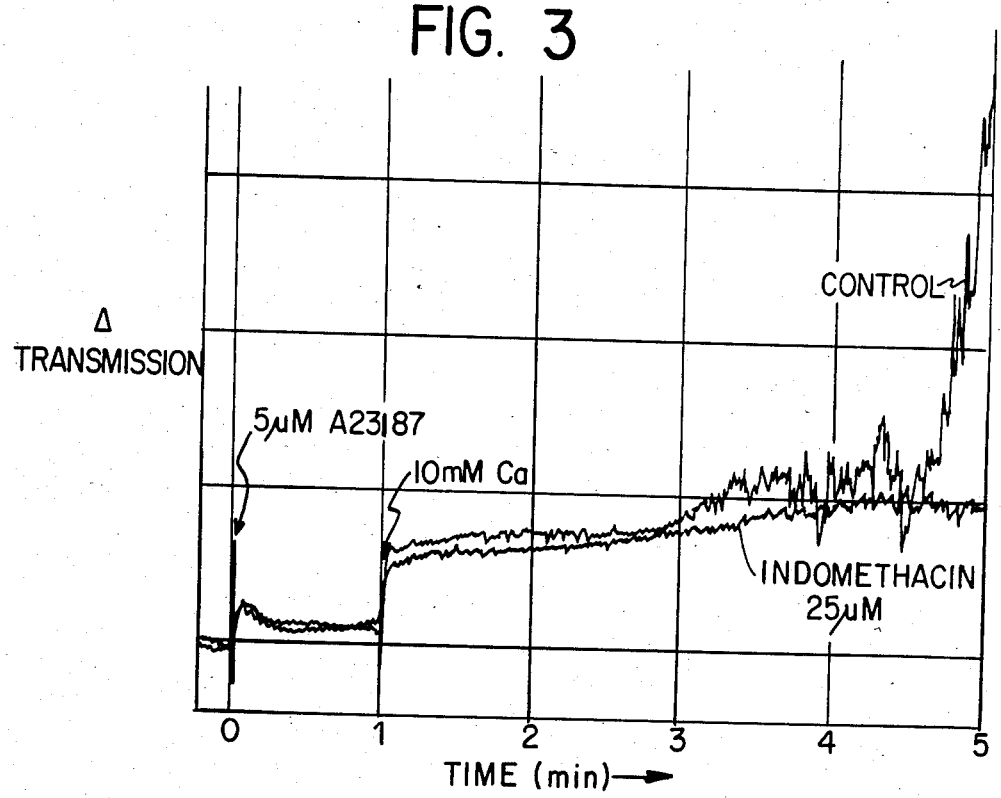

METHOD FOR MEASURING ANTI-INFLAMMATORY PROPERTIES OF A COMPOSITION

The U.S. government has rights in the invention based upon research support in the form of Grant Nos. AM-11949, AI-17365, HL-19721, AM-27851 and AM-28290 from the National Institute of Health.

FIELD OF THE INVENTION

Disclosed herein is a method for in vitro screening of nonsteroidal anti-inflammatory agents by aggregometry of dissociated sponge cells.

BACKGROUND OF THE INVENTION

Inflammation has several characteristic processes including permeability changes in the microvasculature, leakage of the elements of blood into the interstitial spaces, and migration of leukocytes into the inflamed tissue. Chemotactic factors are liberated at the site of inflammation and phagocytic leukocytes (neutrophils) migrate into the area, secreting lysosomal constituents. In addition, to releasing lysosomes, neutrophils exhibit aggregation and superoxide generation when exposed to appropriate stimuli. Neutrophil aggregation has been characteristically associated with inflammation.

A class of compounds known as nonsteroidal anti-inflammatory drugs (NSAIDs) has been widely used to combat inflammation as such drugs do not display the undesirable side effects of the steroidal anti-inflammatory agents. The most common member of this class is aspirin. One of the properties of NSAIDs is their ability to inhibit the aggregation of human neutrophils. Measuring the degree of neutrophil aggregation inhibition caused by these anti-inflammatory agents is a method of screening potentially therapeutic compounds for effectiveness as anti-inflammatory agents because neutrophil aggregation is a characteristic feature of inflammation (the degree of aggregation being proportional to the intensity of inflammation). However, it is difficult and impractical to measure aggregation inhibition of neutrophils directly because the procedure requires the isolation and purification of neutrophils from whole blood, a multistep process which is both time and labor intensive. Moreover, sterile techniques must be used. The procedure requires separating neutrophils from venous anticoagulated blood by sequential Hypaque-Ficol gradient centrifugation, dextran sedimentation, and hypotonic lysis of residual red blood cells.

Therefore, it is desirable to utilize an in vitro model for neutrophil aggregation which can be utilized very economically in time, effort and expense but which also yields reliable results. It is desirable to work under non-sterile conditions. This saves time and labor.

OBJECTS OF THE INVENTION

It is an object of the present invention to provide a simple, inexpensive, rapid and easily standardized method of quantitatively measuring the aggregation of marine sponge cells.

A further object of the present invention is to provide a simple, inexpensive, rapid and easily standardized method for screening potentially efficacious nonsteroidal anti-inflammatory agents. Another object of the present invention is to provide a method for screening non-steroidal anti-inflammatory agents by measuring the degree to which such agents inhibit the aggregation of dissociated marine sponge cells.

A still further object of the present invention is to provide a method of screening anti-inflammatory agents in vitro employing a clinical aggregometer to measure the degree to which such agents inhibit the aggregation of marine sponge cells.

These and other objects of this invention will become apparent to those skilled in the art from the following detailed description of the invention, the accompanying claims and appended drawings.

SUMMARY OF THE INVENTION

It has now been unexpectedly discovered that the marine sponge can serve as an in vitro model for neutrophil aggregation. It has also been discovered that marine sponge cells can be used to determine the relative anti-inflammatory properties of non-steroidal anti-inflammatory pharmaceutical agents and that aggregation of marine sponge cells can be accurately and reliably measured through the use of a clinical aggregometer.

BRIEF DESCRIPTION OF THE DRAWINGS

FIG. 1 is a graph showing the chart recorder tracings of two experiments. The y-axis represents change in light transmission and the x-axis represents time. This graph depicts data regarding the inhibitory effects of piroxicam on marine sponge cells.

FIG. 3 is similar to FIGS. 1 and 2 and shows the effects of indomethacin on marine sponge cells aggregation. A control tracing (without indomethacin) is presented for comparison.

DETAILED DESCRIPTION OF THE INVENTION

Figure 2:
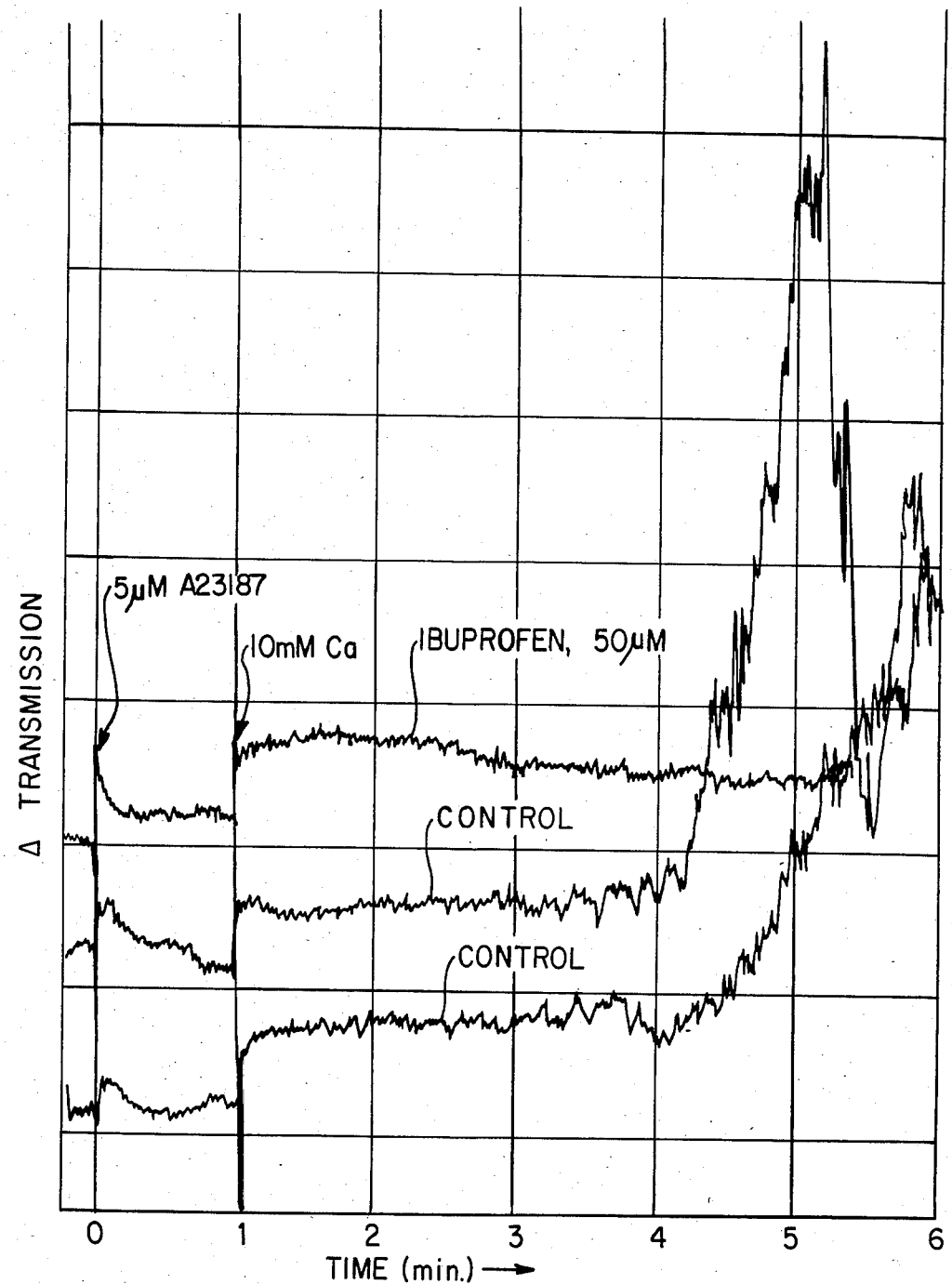
FIG. 2 is a graph similar to FIG. 1 except that three tracings are recorded: one for ibuprofen and two for identical controls.

Neutrophil aggregation may be measured by providing a suspension of dissociated cells, and measuring the change in optical density of the suspension over time. As the motile neutrophils start to aggregate, the optical density of the suspension decreases, as the amount of light transmitted through the suspension increases. The change in optical density is proportional to the degree of aggregation of the neutrophils. Use of a clinical aggregometer makes it possible to determine (1) the rate of neutrophil aggregation; and (2) the extent of neutrophil aggregation on a quantitative basis.

Clinical aggregometry has been used to measure aggregation in human neutrophils (See, e.g., Kaplan, H., Edelson, H., Friedman R. & Weissmann, G., 1982, Biochim. Biophys. Acta, 721, 55–63, and platelets (Born, G. V. R. & Cross, M. J. 1963, J. Physiol., London, 168, 178–195), and in Limulus amoebocytes (Kenney, D. M., Belamarich, F. A., & Shepro, D., 1972 Biol. Bull. 143, 548–567).

Sponge cell aggregation has been studied for more than half a century for the purpose of studying sponge biology. Measurement of sponge cell aggregation has always been qualitative or semi-quantitative in the past. The techniques previously used generally involved visual observation of a suspension of sponge cells after an incubation period and scoring the extent of aggregation semi-quantitatively on an approximate scale of e.g., 0,+,++, +++ and ++++.

As disclosed above, clinical aggregometry has been used for over 20 years as a method for measuring, e.g., human neutrophils, blood platelets and Limulus ameobocytes. However, until the present invention, it had never been used to measure aggregation of marine sponge cells due to the widely held belief that marine sponge cells required a comparatively long incubation period and were relatively slow to aggregate. Marine sponge researchers typically allow a suspension of cells to incubate for long periods (i.e. over 20 minutes or even overnight) before scoring aggregation visually. Using the visual observation technique, many plates can be scored for aggregation in a short period of time. Using a clinical aggregometer, only one sample can be measured at a time and this would result in an unacceptable amount of time spent testing a sample considering the time believed necessary to incubate a sample before aggregation could be measured. Accordingly, use of a clinical aggregometer in marine sponge research was avoided.

The present inventors unexpectedly discovered that a clinical aggregometer may be used in the quantitative determination of aggregation of marine sponge cells, e.g., *Microciona prolifera* (red beard sponge) and that marine sponge cells begin to aggregate much sooner than had been previously believed. In fact, the present inventors discovered that marine sponge cells aggregate at a rate approximately the same as that of human neutrophils. Therefore, sponge cell aggregation can be measured by clinical aggregometry in a few minutes rather than the hours that have been believed necessary in the past.

Further, the present inventors discovered NSAIDs are capable of inhibiting the aggregation of marine sponge cells and human neutrophils to the same degree in an analogous, dosage dependent manner and that, accordingly, marine sponge cell suspensions may be used in screening tests of NSAIDs in the same way as human neutrophil suspensions have heretofore been used. In addition, the effect of said NSAIDs on sponge cell aggregation may be studied and employed as a standard in testing the relative effectiveness of novel nonsteroidal compositions as anti-inflammatory agents.

The clinical aggregometer operates as follows: a suspension of dissociated cells capable of aggregating is maintained as light is passed through the suspension. Initially, there is a low transmission of light through the suspension due to the short mean distance between individual cells (or particles) present in the suspension. A short mean distance implies a high likelihood of the light beam of the aggregometer striking a cell, and being deflected, resulting in less light transmission. As these cells begin to aggregate, more open spaces occur in the suspension, the mean distance between cells increases, there is less probability of deflection, and more light is transmitted through the suspension. The change in light transmission over time can be easily measured on a chart recorder, thereby allowing precise measurement of the rate and extent of aggregation of the cells in suspension.

According to the present invention, an aqueous suspension of dissociated marine sponge cells is prepared in accordance with methods known in the art of marine sponge biology and NSAID neutrophil screening. For purposes of the present invention the cell content of such suspension may be of the order of $10^7$–$10^9$ cells/ml, but preferably remains within $10^7$ cells/ml. The water is preferably sea water essentially free of calcium and magnesium. In addition, resembling neutrophils that aggregate in response to various stimuli, dissociated sponge cells require the presence of an aggregation inducing agent. Such agents include, but are not limited to calcium, calcium ionophores, and specific aggregation factors, and are well known in the art.

Following preparation of the sponge cell suspension, an NSAID or a potential NSAID (i.e. a substance to be tested for anti-inflammatory activity) is introduced therein at a concentration which in the opinion of those skilled in the art such a NSAID, if used, would be present in the human blood stream. For neutrophil cell suspension NSAID screening cell concentrations range between about 1 and 100 $\mu$M. The same NSAID concentration ranges are also appropriate for the present invention.

The aggregation over time of the sponge cells under the influence of NSAID (or without an NSAID if the sample is a control sample) is then measured in a clinical aggregometer, as described above, and the inhibitory action of the NSAID or potential NSAID is determined.

In this manner, standards may be established by testing the effect on sponge cell aggregation of known NSAIDs and subsequently, the behavior of potential NSAIDs may be compared against that of known NSAIDs. Thus, a testing procedure has been devised for the preliminary screening of nonsteroidal compositions as anti-inflammatory agents.

As used herein, light transmission is defined as the capacity of a suspension to transmit or absorb light that has been introduced to it. Light transmission is also defined as the logarithm of the reciprocal of optical density.

Reference is made to the following examples to show the general procedure for quantitatively measuring aggregation of marine sponge cells. These examples are set forth in order to illustrate but not to limit the present invention.

EXAMPLE 1

A sponge cell suspension ($10^7$ cells/ml.) was prepared from *Microciona prolifera* sponge fragments (approximately 1 gram each) which were cut and rinsed for five minutes in 30 ml of ice cold calcium, Magnesium-free sea water (CMFSW) containing EDTA (ethylenediamine tetraacetic acid) (2.5 mM) and 10 mM solution of HEPES (N-2-hydroxy-ethylpiperazine-N'-2-ethanesulfonic acid). The sponge fragments were transferred to 15 ml of CMFSW, whereupon the cells were dissociated mechanically and remaining fragments discarded.

Into round glass cuvettes (45 mm$\times$4 mm) were placed 0.1 ml of the above suspension containing dissociated *Microciona prolifera* cells ($2\times10^8$ ml.) and a metal stirring bar (1 mm$\times$3 mm); the cuvettes and stirring bars had been siliconized (Prosil 28, obtained from PLR Research Chemicals, Gainesville, Fla., diluted 1:100 in distilled water).

The suspensions were stirred at 250 rpm (rpm greater than 900 caused cell death) at room temperture, (22°–24° C.).

Aggregation was measured using a Payton Aggregation Module clinical aggregometer (Payton Associates, Inc., Buffalo, N.Y.) and an Omniscribe chart recorder (Houston Instruments, Houston, Tex.). The cuvettes were placed in the aggregometer and a broad spectrum light source was directed through the suspension. The suspension was maintained by a magnetic stirrer beneath the metal stirring bar contained in the cuvette. Minimum light transmission was set arbitrarily with a cuvette containing 0.1 ml of the cell suspension. Maximum light transmission (full scale deflection of recording pen corresponds to 8 inches) was set with a cuvette containing 0.05 ml of the same cell suspension and 0.05 ml of CMFSW. In this manner the sensitivity was set so that the full scale deflection corresponded to a two fold increase in light transmission (100% ΔT).

Using a transducer to express changes in light transmitted through the suspension, the chart recorder provided a graph displaying changes in optical density over time. Maximum average aggregation obtained was 90% (judged by light microscopy) and was dependent on such factors as cell viability, ion concentration and stirring bar speed (rpm). Since changes in optical density are expressed two dimensionally with time, it is possible to determine the rate as well as the extent of aggregation for a given suspension of cells at a given ion concentration and stirring bar speed.

Using the quantitative aggregation determination method described above, the effect of NSAIDs on marine sponge cell aggregation was tested using three different drugs. These drugs, which inhibit neutrophil aggregation in humans, presumably by blocking Ca-dependent reactions, were found to inhibit aggregation of Microciona cells as well to the same extent.

EXAMPLE 2

Using the procedure of Example 1, the effect of the NSAID piroxicam on marine sponge cell aggregation was determined (see FIG. 1). 10 μl of an 0.5 mM solution of piroxicam (obtained from Pfizer, Groton, Conn.) were added to the suspension of sponge cells. At an initial time, T=0, the suspension was preincubated by adding 5 μl of a 1 mM solution of a calcium ionophore, A-23187, obtained from Sigma, St. Louis, to the solution. One minute later, T=1, 5 μl of a 100 mM solution of $CaCl_2$ were introduced. Preincubation with an aggregation inducing factor such as a calcium ionophore and/or calcium ion is necessary to induce the sponge cells to aggregate. Subsequent changes were recorded until approximately T=4.5 min. This experiment was also performed without the piroxicam to serve as a control, as shown in the lower tracing of FIG. 1.

The results of this experiment clearly indicate that piroxicam inhibits marine sponge cell aggregation. In the control (without piroxicam), light transmission increased approximately 4.0 units after the addition of calcium to the solution. On the other hand, the suspension containing piroxicam showed an increase on only 1.1 units at T=4.5. As explained above, a change in light transmission is directly proportional to cell aggregation. An increase in light transmission (decrease in optical density) implies an increase in the amount of cell aggregation. Therefore, the cell suspension containing piroxicam inhibited aggregation approximately 73% compared to the control suspension without piroxicam.

EXAMPLE 3

The experiment of Example 2 was conducted using 10 μl of an 0.5 mM solution of ibuprofen as the NSAID (obtained from Upjohn, Kalamazoo, Mich.). In this Example, 5 μl of a 1 mM solution of ionophore A23187 was provided at the initiation of the experiment and 10 μl of 100 mM solution of $CaCl_2$ was added at T=1. Two identical controls (without ibuprofen) were also charted to show normal Microciona aggregation. FIG. 2 reveals the dramatic inhibitory effect (approximately 99% at T=5 minutes) of ibuprofen under these conditions on sponge cell aggregation.

EXAMPLE 4

The experiment of Example 3 was conducted using 5 μl of an 0.5 mM solution of indomethacin as the NSAID (obtained from Merck, Rahway, N.J.). In this Example, calcium was provided as 5 μl of 1 mM of calcium ionophore A23187 and 10 μl of 100 mM Ca solution. The results of this experiment are shown in FIG. 3.

Here again, aggregation inhibition is clearly shown. After initial equilibration, the indomethacin tracing exhibits an increase in light transmission of only 0.5 units in 4 minutes. The control on the other hand, showed an increase of approximately 4.0 units during the 4 minute incubation period. This corresponds to approximately 87% aggregation inhibition.

What is claimed is:

1. A method for measuring the anti-inflammatory properties of a composition by measuring the effect of the composition on marine sponge cell aggregation comprising:
   (i) adding a predetermined amount of a composition to an aqueous suspension of dissociated marine sponge cells;
   (ii) measuring the optical density of said suspension after a first predetermined time interval;
   (iii) measuring the optical density of said suspension at a second predetermined time after said first time;
   (iv) measuring the effect of the composition on marine sponge cell aggregation by comparing the optical density at said first time with the optical density at said later time as a measure of the anti-inflammatory properties of the composition.

2. The method of claim 1 wherein marine sponge cell aggregation is measured by use of a clinical aggregometer.

3. The method of claim 1 wherein said suspension additionally comprises sea water essentially free of calcium and magnesium and a calcium ion-containing solution introduced therein, prior to optical density measurements, as an aggregation inducing factor.

4. The method of claim 1 wherein said suspension additionally comprises a calcium ionophore as an aggregation inducing factor.

5. A method for measuring anti-inflammatory properties of a composition comprising:
   (i) adding a predetermined amount of a composition to a suspension of dissociated marine sponge cells that are capable of aggregation;
   (ii) measuring a change in optical density of said suspension by comparing the optical density of the suspension measured at an initial time to the optical density of the suspension measured at a later time;
   (iii) measuring aggregation inhibition caused by exposing the dissociated marine sponge cells to said composition by comparing the change in optical density to the change in optical density obtained with a control not containing said composition; and
   (iv) measuring the anti-inflammatory properties of said composition by comparing the aggregation inhibition in step (iii) to the aggregation inhibition measured by carrying out steps (i)–(iii) using a known non-steroidal anti-inflammatory agent in place of said composition.

6. The method of claim 5, wherein said known anti-inflammatory agent is selected from the group consisting of piroxicam, ibuprofen and indomethacin.

* * * * *